(12) United States Patent
Jennewein

(10) Patent No.: US 9,968,625 B2
(45) Date of Patent: May 15, 2018

(54) SYNTHETIC OR RECOMBINANT FUCOSYLATED OLIGOSACCARIDES FOR USE IN THE TREATMENT OF INFECTIONS

(71) Applicant: Jennewein Biotechnologie GmbH, Rheinbreitbach (DE)

(72) Inventor: Stefan Jennewein, Bad Honnef (DE)

(73) Assignee: Jennewein Biotechnologie GmbH, Rheinbreitbach (DE)

( * ) Notice: Subject to any disclaimer, the term of this patent is extended or adjusted under 35 U.S.C. 154(b) by 50 days.

(21) Appl. No.: 14/830,558

(22) Filed: Aug. 19, 2015

(65) Prior Publication Data

US 2015/0352133 A1    Dec. 10, 2015

Related U.S. Application Data

(63) Continuation of application No. PCT/EP2014/052912, filed on Feb. 14, 2014.

(30) Foreign Application Priority Data

Feb. 21, 2013   (EP) .................................... 13156224

(51) Int. Cl.
 *A61K 31/702*   (2006.01)
 *A61K 31/715*   (2006.01)

(52) U.S. Cl.
 CPC .......... *A61K 31/702* (2013.01); *A61K 31/715* (2013.01)

(58) Field of Classification Search
 None
 See application file for complete search history.

(56) References Cited

U.S. PATENT DOCUMENTS 5,945,314 A    8/1999   Prieto et al.

FOREIGN PATENT DOCUMENTS

| JP | 2002-218992 A | 8/2002 |
|---|---|---|
| WO | WO 1991/16449 | 10/1991 |
| WO | WO 2005/055944 A2 | 6/2005 |
| WO | WO 2005/055944 A3 | 6/2005 |
| WO | WO 2010/120682 A1 | 10/2010 |
| WO | WO 2012/092153 A1 | 7/2012 |

OTHER PUBLICATIONS

Nilsson, J. et al., Glycoconj. J., "Norwalk virus-like particles bind specifically to A, H and difucosylated Lewis but not to B histo-blood group active glycosphingolipids", 2009, vol. 26, pp. 1171-1180.*
"Prevent", WordNet Search 3.0, also available at http://wordnet.princeton.edu; retrieved Nov. 2007.*
Drouillard, S. et al., Angew. Chem. Int. Ed., "Large-Scale Synthesis of H-Antigen Oligosaccharides by Expressing Helicobacter pylori alpha1,2-Fucosyltransferase in Metabolically Engineered *Escherichia coli* Cells", 2006, vol. 45, pp. 1778-1780 (Year: 2006).*
Morrow et al., "Human milk oligosccharides are associated with protection against diarrhea in breast-fed infants," *J. Pediatr.* 145:297-303 (2004).
International Search Report and Written Opinion from parent PCT Application No. PCT/EP2014/052912, 10 pages, (dated Mar. 31, 2014).
Notification of Reasons for Rejection issued in corresponding Japanese Patent Application No. 2015-558404, dated Mar. 13, 2018, and an English translation thereof.

* cited by examiner

*Primary Examiner* — Layla D Berry
*Assistant Examiner* — Bahar Craigo
(74) *Attorney, Agent, or Firm* — Klarquist Sparkman, LLP

(57) ABSTRACT

The present invention relates to synthetic fucosylated oligosaccharide for use in the treatment or prophylaxis of an infection with a Norwalk-like Virus or Rotavirus of a mam-mal, wherein the synthetic fucosylated oligosaccharide comprises a non-reducing end and an reducing end, wherein the reducing end comprises a first carbohydrate unit consisting of a galactose (Gal) linked via a β1-4 glycosidic bond to a glucose (Glc), and wherein the non-reducing end comprises a second carbohydrate unit linked via a β1-3 glycosidic bond to the first carbohydrate unit of the reducing end, and wherein the second carbohydrate unit comprises a) at least one or more of a fucose (Fucose) and a Galactose (Gal), and b) at least one or more of a N-acetylglucosamine (GlcNAc) or a N-acetylgalactosamine (GalNAc).

15 Claims, 2 Drawing Sheets

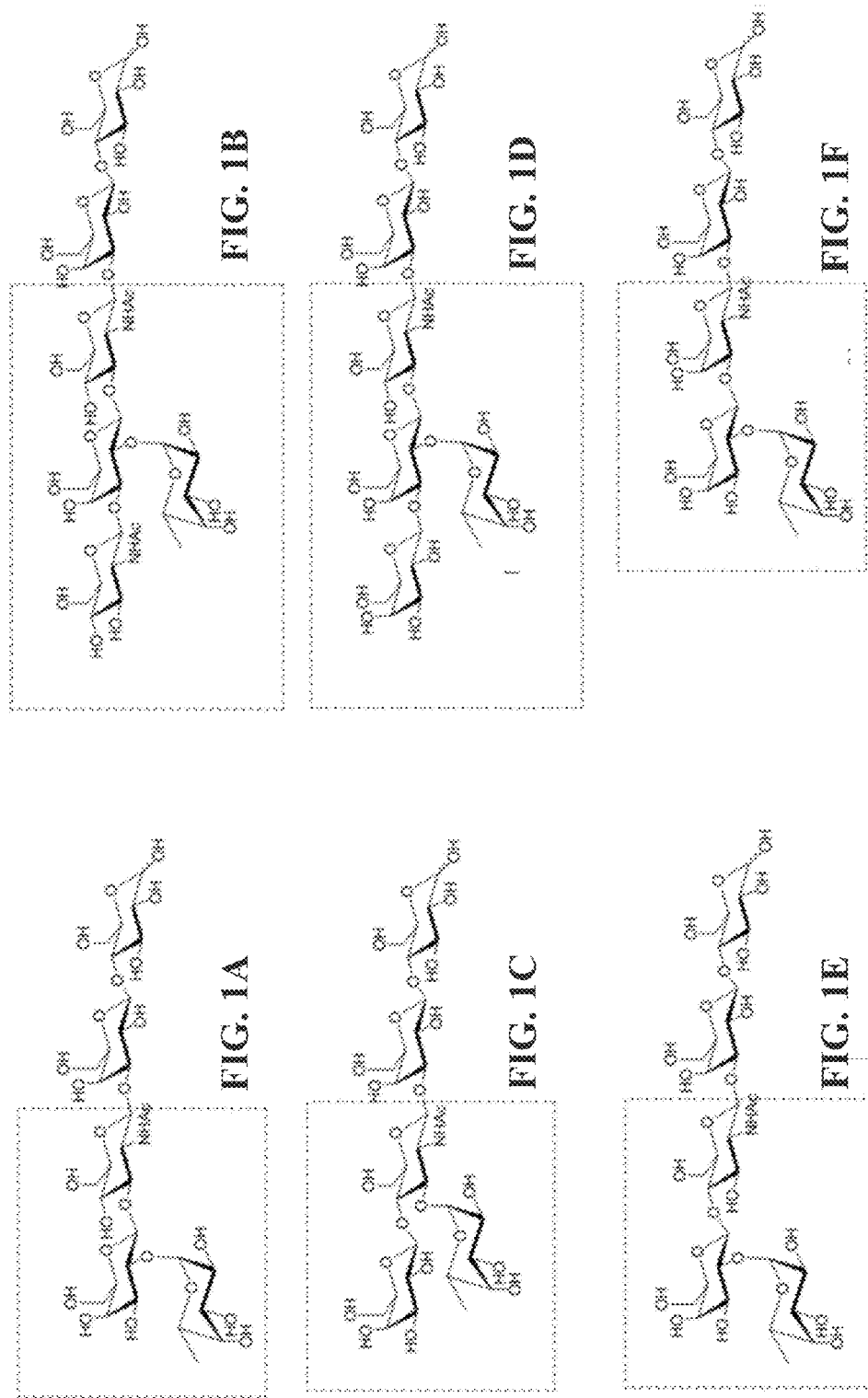

Pathogen connects to surface-bound sugar

Elimination of pathogen. No infection

SYNTHETIC OR RECOMBINANT FUCOSYLATED OLIGOSACCARIDES FOR USE IN THE TREATMENT OF INFECTIONS

CROSSREFERENCES TO RELATED APPLICATIONS

This application is a continuation of international patent application PCT/EP2014/052912, filed on Feb. 14, 2014, designating the U.S., which international patent application has been published in the English language and claims priority to European patent application EP 13156224.1, filed on Feb. 21, 2013. The entire contents of these priority applications are incorporated herein by reference.

BACKGROUND OF THE INVENTION

The present invention relates to synthetic or recombinant fucosylated oligosaccharides for use in the treatment or prophylaxis of an infection with a Norwalk-like Virus or a Rotavirus of a mammal.

The Norwalk-like viruses (NLV), also called Noroviruses, are non-enveloped viruses belonging to the calicivirus family. They are the most common cause of viral acute gatroenteritis in humans, and affect people of all age. The viruses are transmitted by fecally-contaminated food or water, by person-to-person contact, and via aerosolization of the virus and subsequent contamination of surfaces. An infection with Noroviruses is characterized by nausea, forceful vomiting, watery diarrhea, and abdominal pain. In particular very young children, elderly persons, and persons with weakened immune system are often in danger of dying when heavily infected. Noroviruses are highly contagious, and already few virus particles can cause an infection, which explains the rapid and excessive spread of the virus and of infected people. Also, due to their high resistance towards cleaning agents, Norovirus-breakouts are regularly observed in schools, clinics, senior homes, children day care centers, etc.

Norovirus-infections and their symptoms represent one of the most common causes of death worldwide for children under the age of three. In Germany, more than 15.000 infections have been reported for infants (age 0 to 12 months) in the year 2011 alone; with about 20 millions infections worldwide, more than 200.000 cases of death of infants are estimated to be caused by a Norovirus-infections.

While Norovirus-studies remain difficult due to the fact that no animal models exist, there has recently been developed a cell culture model for assessing their pathogenicity. Also, using recombinant virus particles and testing volunteers, the histo-blood groups antigens (abbreviated with HBGA) serving as receptors for Noroviruses have been identified. HBGA are complex oligosaccharides which are expressed on the surface of red blood cells, the gastric mucosa, of the respiratory passages, urogenital system and of the intestinal tract. The HBG antigen H1, which is encoded via FUC2, an alpha-1,2-fucosyltransferase, has been identified as the most important genetic predisposition: individuals with homozygous zero-mutant alleles for FUC2 have been shown as being resistant towards gastrointestinal infections of the Norovirus.

Although other studies have shown that up to 90% of the adults tested so far do have antibodies against Noroviruses, it has also been found out that the immunity lasts only as short as about 6 months, and, thus does not provide protection even against a reinfection with the same infectious strain.

Up to today, there is neither a vaccine available nor a causal therapy or a causal cure for norovirus-gastroenteritis; as a consequence, treatment of Norovirus-gastroenteritis is restricted to a supportive oral and eventually parenteral rehydration with electrolytes.

Similarly, infections with Rotavirus are the most common cause of severe diarrhea among infants and young children. Rotavirus is a genus of double-stranded RNA virus belonging to the Reoviridae family. By the age of five, nearly every child in the world has been infected with rotavirus at least once. As the Norovirus, the Rotavirus is transmitted by the fecal-oral route.

Rotavirus is usually an easily managed disease of childhood, but worldwide more than 450,000 children under five years of age still die from rotavirus infection each year, most of whom live in developing countries, and almost two million more become severely ill. Although the incidence and severity of rotavirus infections has declined in countries that have added rotavirus vaccine to their routine childhood immunisation policies, a vaccine that prevents infection of both, Norovirus and Rotavirus, would be highly valuable.

Marionneau et al. ("Norwalk Virus Binds to Histo-Blood Group Antigens Present on Gastroduodenal Epithelial Cells of Secretor Individuals", Gastroenterology (2002) 122: 1967-1977), have shown that recombinant Norwalk-virus-like particles use carbohydrates present on human gastroduodenal epithelial cells as ligands.

Further, Morrow et al. ("Human Milk Oligosaccharides are associated with protection against Diarrhea in Breast-fed Infants", J. Pediatr. (2004) 145:297-303) have observed that Campylobacter and Calicivirus caused diarrhea occurred less often in infants who have been fed with milk containing high levels of 2-linked fucosyloligosaccharide as a percent of milk oligosaccharide.

In this connection, WO 2005/055944 discloses the use of oligosaccharide compositions, in particular of glycoproteins where 2-fucosyllactose is linked to human serum albumin, in the treatment of infections.

Although, with the above background, there are currently different approaches to treat or prevent infections with Noroviruses, no actual vaccine or composition has been provided yet that would have proven effective in such treatment/prophylaxis.

Thus, there still is a need for novel substances and compositions by means of which a Norovirus-infection can efficiently be treated or prevented, and it is an object of the invention to provide such a substance or composition containing such substance.

SUMMARY OF THE INVENTION

This and other objects are solved by a substances as set forth in the outset, wherein the synthetic or recombinant fucosylated oligosaccharide comprises a non-reducing end and an reducing end, wherein the reducing end comprises a first carbohydrate unit consisting of a galactose (Gal) linked via a β1-4 glycosidic bond to a glucose (Glc), and wherein the non-reducing end comprises a second carbohydrate unit linked via a β1-3 glycosidic bond to the first carbohydrate unit of the reducing end, and wherein the second carbohydrate unit comprises a) at least one or more of a fucose (Fuc) and a Galactose (Gal), and b) at least one or more of a N-acetylglucosamine (GlcNAc) or a N-acetylgalactosamine (GalNAc), and wherein the second carbohydrate unit is selected of one of the following: Fucα1-2Galβ1-3GlcNAc, GlcNAcα1-3 (Fucα1-2)Galβ1-3GlcNAc, Galβ1-4(Fucα1-

3)GlcNAc, Galβ1-3(Fucα1-2)Galβ1-3GlcNAc, Fucα1-2Galβ1-4GlcNAc, Fucα1-2Galβ1-4GalNAc.

BRIEF DESCRIPTION OF THE DRAWINGS

Several embodiments of the invention are illustrated in the figures and explained in more detail in the following description. In the figures:

FIGS. 1A-1F shows the synthetic oligosaccharides of the present invention; in particular Fucα1-2Galβ1-3GlcNAcβ1-3Galβ1-4Glc (A), GlcNAcα1-3 (Fucα1-2)Galβ1-3GlcNAcβ1-3Galβ1-4Glc (B), Galβ1-4(Fucα1-3)GlcNAcβ1-3Galβ1-4Glc (C), Galβ1-3(Fucα1-2)Galβ1-3GlcNAcβ1-3Galβ1-4Glc (D), Fucα1-2Galβ1-4GlcNAcβ1-3Galβ1-4Glc (E), Fucα1-2Galβ1-4GalNAcβ1-3Galβ1-4Glc (F).

DESCRIPTION OF PREFERRED EMBODIMENTS

Figure 2A:
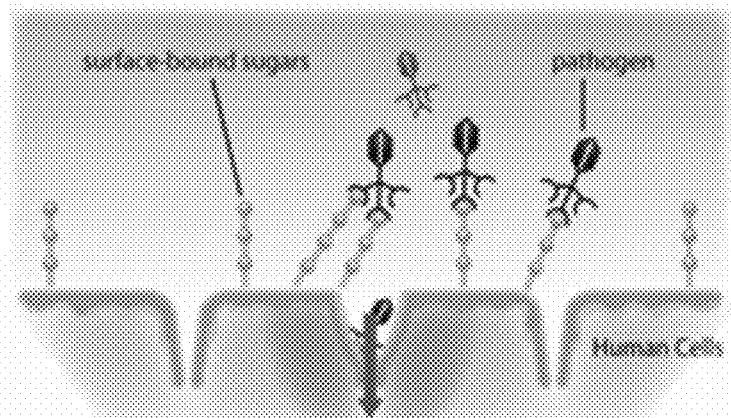
FIGS. 2A-2B a schematic drawing of the mechanism of action of the oligosaccharides of the present invention; (A) shows a virus-infection without treatment/prevention with the oligosaccharides of the present invention; and (B) shows the protection from infection by the oligosaccharides of the invention.

According to a preferred embodiment, it is particularly preferred if the oligosaccharide is selected from at least one of the followings: Fucα1-2Galβ1-3GlcNAcβ1-3Galβ1-4Glc; GlcNAcα1-3 (Fucα1-2)Galβ1-3GlcNAcβ1-3Galβ1-4Glc; Galβ1-4(Fucα1-3)GlcNAcβ1-3Galβ1-4Glc; Galβ1-3 (Fucα1-2)Galβ1-3GlcNAcβ1-3Galβ1-4Glc; Fucα1-2Galβ1-4GlcNAcβ1-3Galβ1-4Glc; Fucα1-2Galβ1-4GalNAcβ1-3Galβ1-4Glc.

Further, the invention relates to a combination of at least two, three, four, five or six of the fucosylated oligosaccarides as mentioned above.

The term "Oligosaccharide", as it is used herein and as generally understood in the state of the art, refers to a saccharide polymer containing a small number, typically three to ten, of simple sugars, i.e. monosaccharides. Accordingly, a "fucosylated oligosaccharide", is a saccharide polymer comprising a fucose residue.

The expression "carbohydrate unit", as it is used herein, is to be understood as a saccharide unit comprising two or more monosaccharides linked with each other via glycosidic bonds. Accordingly, the expressions "carbohydrate" or "saccharide" are synonymously used herein.

Accordingly, the inventions also relates to a pharmaceutical composition comprising at least one of the synthetic fucosylated oligosaccharides as outlined above and a pharmaceutically acceptable carrier.

When preparing the pharmaceutical compositions of the present invention, the active ingredient, i.e. the oligosaccharide of the invention, will usually be mixed with a carrier, or diluted by a carrier or enclosed within a carrier. Dosage unit forms or pharmaceutical compositions include tablets, capsules, pills, powders, granules, aqueous and non-aqueous oral solutions and suspensions, and parenteral solutions. Also, dosage unit forms can be provided, which may be adapted for various methods of administration, including controlled release formulations, such as subcutaneous implants. Administration methods include oral, rectal, parenteral (e.g., intramuscular, intraperitoneal, intravenous, intracisternal injection or infusion, subcutaneous injection, or implant), inhalation spray, nasal, sublingual, or topical routes of administration. Also, the pharmaceutical compositions and/or of the oligosaccharide according to the invention can be enterally administered via the gastro-intestinal tract of a patient, e.g. via a gastric tube, according to a preferred embodiment of the invention.

Parenteral formulations include pharmaceutically acceptable aqueous or non-aqueous solutions, dispersion, suspensions, emulsions, and sterile powders for the preparation thereof. Examples of carriers include water, ethanol, polyols (propylene glycol, polyethylene glycol), vegetable oils, and injectable organic esters such as ethyl oleate. Carriers for solid dosage forms include fillers or extenders, binders, humectants, disintegrating agents, solution retarders, absorption accelerators, adsorbants, lubricants, buffering agents, and propellants.

Compositions may also contain adjuvants such as preserving, wetting, emulsifying, and dispensing agents; antimicrobial agents such as parabens, chlorobutanol, phenol, and sorbic acid; isotonic agents such as a sugar or sodium chloride; absorption-prolonging agents such as aluminum monostearate and gelatin; and absorption-enhancing agents.

It is not intended that the present invention be limited to particular formulations or particular modes of administration. In one embodiment, the composition is formulated for oral administration, and the pharmaceutical composition can be formulated for oral administration in a dosage containing an amount of the oligosaccharide of the invention that ranges from about 0.1 to about 20 mg/kg per day.

Also, such pharmaceutical compositions can be formulated in a solid or liquid dosage form. For example, the pharmaceutical compositions may be formulated as a solid in the form of tablets, capsules, granules, powders, and similar compounds. The pharmaceutical compositions may also be formulated as a liquid in the form of syrups, injection mixtures, and the like.

Such pharmaceutical compositions can also be present in a kit together with an instruction means for administering the composition.

According to another embodiment of the present invention, a synthetic nutrition composition is provided comprising at least one of the synthetic fucosylated oligosaccharides according to the invention and as outlined claimed in the attached claims.

The pharmaceutical composition and/or the nutrition composition preferably comprise the synthetic oligosaccharides according to the invention in an amount of about 0.001 mg/mL to about 15 mg/mL.

It is noted that numerical ranges as above and as used herein are intended to include every number and subset of numbers within that range, whether specifically disclosed or not.

The term "nutritional composition" as used herein is used to refer to synthetic formulas including nutritional liquids, nutritional powders, nutritional semi-solids, nutritional semi-liquids, nutritional supplements, and any other nutritional food product as known in the art, and the nutritional powders may be reconstituted to form a nutritional liquid. The mentioned compositions are suitable for oral consumption by a human, and do not include human breast milk or purified components from human breast milk.

The nutritional composition of the invention—as well as the pharmaceutical composition of the invention—may comprise one or more of the oligosaccharides of the invention. As such, the compositions of the invention may comprise two, three, four, five or six of the oligosaccharides of the invention. The compositions of the inventions may also comprises the same or different amount of the oligosaccharides of the invention, and one skilled in the art can—e.g.

depending on the blood group, the age, the weight and overall condition of the object to be treated—readily assess, which of the mentioned oligosaccharides should be used in which amount.

The term "synthetic or recombinant fucosylated oligosaccharide" does specifically exclude fucosylated oligosaccharides purified from human milk, and specifically and only encompasses the fucosylated oligosaccharides of the invention that have been synthesized chemically or by fermentation using a recombinant microorganism. An exemplary way for producing the synthetic oligosaccharides of the invention is by chemical synthesis, bioorganic synthesis using isolated enzymes (fucosyltransferases, galactosyltransferases, N-acetylglkucosaminyltransferases etc.) or a total fermentation employing a recombinant microorganism expressing the required glycosyltransferases for the synthesis of the fucosylated oligosaccharides according to the invention.

The invention also relates to a method for treating or reducing the risk of infection with a Norwalk-like Virus in a mammal, the method comprising the step of administering the synthetic fucosylated oligosaccharide of the invention, or the pharmaceutical composition of the invention, or the synthetic nutrition composition of the invention in a therapeutic effective amount to an object in need thereof.

The subject in need thereof may be an adult, infant, toddler, or child in need thereof. Also, the oligosaccharide of the invention or a mixtures of two or more of the oligosaccharides disclosed herein—be it administered as such, i.e. without any additional components or be it comprised in a composition—may be administered in an amount from about 0.001 mg/mL to about 15 mg/mL.

The pharmaceutical and nutritional compositions and methods may comprise, consist of, or consist essentially of the essential elements of the compositions and methods as described herein, as well as any additional or optional element described herein or otherwise useful in nutritional product applications.

All references to singular characteristics or limitations of the present disclosure shall include the corresponding plural characteristic or limitation, and vice versa, unless otherwise specified or clearly implied to the contrary by the context in which the reference is made.

The present invention utilizes the fact that, in human body, the disclosed novel oligosaccharides bind to the same receptors that Noroviruses and Rotaviruses bind to, and that the oligosaccharides, as a consequence, inhibit binding of the Noroviruses and Rotaviruses to the receptors.

Thus, when present in the human body, the oligosaccharides of the present invention bind to the Noro- or Rotavirus the human body has been infected with, and form an oligosaccharide-virus-complex. Due to the fact that the novel oligosaccharides block the receptors of the Noro-/Rotavirus by means of which receptors the Noro/Rotavirus would otherwise bind to the human cells—and subsequently enter the cell—attachment of the Noro- and/or Rotavirus to human cells is blocked/inhibited and consequently the internalization of the Noro-/Rotavirus is efficiently prevented.

Thus, the novel synthetic oligosaccharides presented herein provide an effective tool for the protection from Noro- and Rotavirus infections, and may be used in either treatment of an acute infection or for a vaccination against a Noro- and/or Rotavirus infection.

Further advantages follow from the description of the embodiments and the attached drawings.

It goes without saying that the abovementioned features and the features which are still to be explained below can be used not only in the respectively specified combinations, but also in other combinations or on their own, without departing from the scope of the present invention.

Examples

FIG. 1 depicts the six oligosaccharides which are used as examples in the treatment or prophylaxis of a Norovirus- and/or Rotavirus infection, with Fucα1-2Galβ1-3GlcNAcβ1-3Galβ1-4Glc being depicted in FIG. 1A, GlcNAcα1-3 (Fucα1-2)Galβ1-3GlcNAcβ1-3Galβ1-4Glc being depicted in FIG. 1B, Galβ1-4(Fucα1-3)GlcNAcβ1-3Galβ1-4Glc being depicted in FIG. 1C, Galβ1-3(Fucα1-2)Galβ1-3GlcNAcβ1-3Galβ1-4Glc being depicted in FIG. 1D, Fucα1-2Galβ1-4GlcNAcβ1-3Galβ1-4Glc being depicted in FIG. 1E, and Fucα1-2Galβ1-4GalNAcβ1-3Galβ1-4Glc being depicted in FIG. 1F. In the formulas, Gal represents a galactose monosaccharide unit, Glc represents a glucose monosaccharide unit, and GalNAc represents an N-acylated galactosamine monosaccharide unit and GlcNAc a glucosamine monosaccharide unit.

The glycosidic bonds between the monosaccharide units of the oligosaccharides of the invention are exemplary outlined for the oligosaccharide depicted in FIG. 1A: In the structure of the oligosaccharide depicted in FIG. 1A, the monosaccharide units are linked as follows: a fucose is linked via a alpha 1→2 glycosidic bond to a galactose which is linked via a beta 1→3 glycosidic bond to a N-acetylglucosamine which is linked via a beta 1→3 glycosidic bond to a galactose which is linked via a beta 1→4 glycosidic bond to a glucose.

In the structure of the oligosaccharide depicted in FIG. 1B, the monosaccharide units are linked as follows: a N-acetylglucosamine is linked via an alpha 1→3 glycosidic bond to a galactose onto which also a fucose is linked via an alpha 1→2 glycosidic bond. Further, the galactose is linked via a beta 1→3 glycosidic bond to a N-acetylglucosamine which is linked via a β1-3 glycosidic bond to a galactose which is linked via a beta 1→4 glycosidic bond to a glucose.

In the structure of the oligosaccharide depicted in FIG. 1C, a galactose is linked via a beta 1→4 glycosidic bond to a N-acetylglucosamine onto which also a fucose is linked via an alpha 1→3 glycosidic bond. The N-acetylglucosamine is linked via a beta 1→3 glycosidic bond to a galactose which is linked via a beta 1→4 glycosidic bond to a glucose.

In the structure of the oligosaccharide depicted in FIG. 1D, a galactose is linked via a beta 1→3 glycosidic bond to a galactose, onto which also a fucose is linked via an alpha 1→2 glycosidic bond. The galactose is linked via a beta 1→3 glycosidic bond to N-acetylglucosamine which is linked via a beta 1→3 glycosidic bond to a galactose which is linked via a beta 1→4 glycosidic bond to a glucose.

In the structure of the oligosaccharide depicted in FIG. 1E, a fucose is linked via an alpha 1→2 glycosidic bond to a galactose which is linked via a beta 1→4 glycosidic bond to N-acetylglucosamine which is linked via a beta 1→3 glycosidic bond to a galactose which is linked via a beta 1→4 glycosidic bond to a glucose.

In the structure of the oligosaccharide depicted in FIG. 1F, a fucose is linked via an alpha 1→2 glycosidic bond to a galactose which is linked via a beta 1→4 glycosidic bond to a N-acetylgalactosamine which is linked via a beta 1→3 glycosidic bond to a galactose which is linked via a beta 1→4 glycosidic bond to a glucose.

The oligosaccharides according to the invention are obtained by fermentation from a simple carbon source (e.g. glycerol, glucose or sucrose) and lactose using a recombinant microorganism; alternatively the oligosaccharides can be obtained by enzymatic synthesis using isolated enzymes (or whole cells), and administered to a patient.

The mode of action of the oligosaccharides of the invention is depicted in FIG. 2: As can been taken from FIG. 2A, the infection with the Norovirus/Rotavirus is manifested in persons not treated with the oligosaccharides of the invention since the Norovirus-/Rotavirus particles can bind to their receptors of human cells.

Figure 2B:
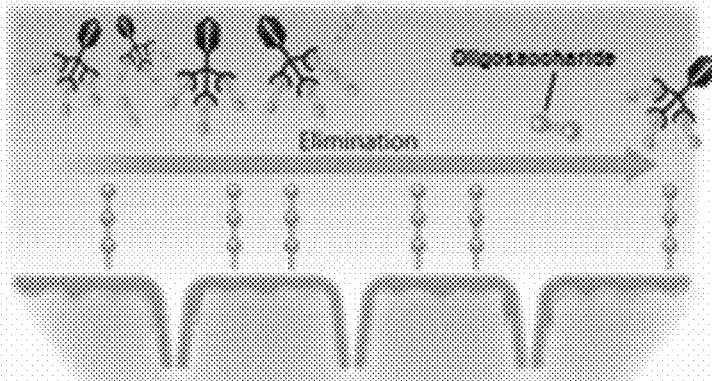

On the other hand, and this is depicted in FIG. 2B, in a person that has been treated with the oligosaccharides of the invention, the Norovirus/Rotavirus cannot bind to their receptors on the surfaces of human cells, since the respective binding sites of the Norovirus/Rotavirus are occupied or blocked by the oligosaccharides of the invention, thus prohibiting the Norovirus/Rotavirus binding to the human cells.

Thus, with the oligosaccharides of the invention, a Norovirus/Rotavirus infection can efficiently be prevented and/or treated.

What is claimed is:

1. A fucosylated oligosaccharide for treating or inhibiting an Norwalk-like Virus or Rotavirus infection in a mammal, wherein the fucosylated oligosaccharide comprises a non-reducing end and a reducing end, wherein the reducing end comprises a first carbohydrate unit consisting of a galactose (Gal) linked via a β1-4 glycosidic bond to a glucose (Glc), and wherein the non-reducing end comprises a second carbohydrate unit linked via a β1-3 glycosidic bond to the first carbohydrate unit of the reducing end, and wherein the second carbohydrate unit comprises a) at least one or more of a fucose (Fuc) and a galactose (Gal), and b) at least one or more of a N-acetylglucosamine (GlcNAc) or a N-acetylgalactosamine (GalNAc), and wherein the second carbohydrate unit is:

GlcNAcα1-3 (Fucα1-2)Galβ1-3GlcNAc

Galβ1-3(Fucα1-2)Galβ1-3GlcNAc or

Fucα1-2Galβ1-4GalNAc.

2. The fucosylated oligosaccharide of claim 1, wherein the fucosylated oligosaccharide is:

GlcNAcα1-3 (Fucα1-2)Galβ1-3GlcNAcβ1-3Galβ1-4Glc.

3. The fucosylated oligosaccharide of claim 1, wherein the fucosylated oligosaccharide is Galβ1-3(Fucα1-2)Galβ1-3GlcNAcβ1-3Galβ1-4Glc.

4. The fucosylated oligosaccharide of claim 1, wherein the fucosylated oligosaccharide is Fucα1-2Galβ1-4GalNAcβ1-3Galβ1-4Glc.

5. A composition comprising two or more of:

GlcNAcα1-3 (Fucα1-2)Galβ1-3GlcNAcβ1-3Galβ1-4Glc;

Galβ1-3(Fucα1-2)Galβ1-3GlcNAcβ1-3Galβ1-4Glc; and

Fucα1-2Galβ1-4GalNAcβ1-3Galβ1-4Glc.

6. A composition comprising the fucosylated oligosaccharide of claim 1, and one or both of Fucα1-2Galβ1-3GlcNAcβ1-3Galβ1-4Glc and Galβ1-4(Fucα1-3)GlcNAcβ1-3Galβ1-4Glc.

7. A pharmaceutical composition comprising at least one of the fucosylated oligosaccharides of claim 1, and a pharmaceutically acceptable carrier.

8. A synthetic nutrition composition comprising at least one of the fucosylated oligosaccharides of claim 1.

9. A method for treating a Norwalk-like Virus infection in a mammal, comprising administering a therapeutically effective amount of the fucosylated oligosaccharide of claim 1 to the mammal, thereby treating the Norwalk-like virus infection in the mammal.

10. A method for treating a Norwalk-like Virus infection in a mammal, comprising administering a therapeutically effective amount of the fucosylated oligosaccharide of claim 2 to the mammal, thereby treating the Norwalk-like virus infection in the mammal.

11. A method for treating a Norwalk-like Virus infection in a mammal, comprising administering a therapeutically effective amount of the fucosylated oligosaccharide of claim 3 to the mammal, thereby treating the Norwalk-like virus infection in the mammal.

12. A method for treating a Norwalk-like Virus infection in a mammal, comprising administering a therapeutically effective amount of the fucosylated oligosaccharide of claim 4 to the mammal, thereby treating the Norwalk-like virus infection in the mammal.

13. A method for treating a Norwalk-like Virus infection in a mammal, comprising administering a therapeutically effective amount of the composition of claim 5 to the mammal, thereby treating the Norwalk-like virus infection in the mammal.

14. A method for treating a Norwalk-like Virus infection in a mammal, comprising administering a therapeutically effective amount of the pharmaceutical composition of claim 7 to the mammal, thereby treating the Norwalk-like virus infection in the mammal.

15. A method for treating a Norwalk-like Virus infection in a mammal, comprising administering a therapeutically effective amount of the synthetic nutrition composition of claim 8 to the mammal, thereby treating the Norwalk-like virus infection in the mammal.

* * * * *